United States Patent [19]
Arretz et al.

[11] Patent Number: 5,442,123
[45] Date of Patent: Aug. 15, 1995

[54] PROCESS FOR SELECTIVELY PREPARING ORGANIC TRISULFIDES

[75] Inventors: Emmanuel F. Arretz, rue de Cagnes, France; Glenn T. Carroll, Jeffersonville; Roger T. Clark, Pottstown, both of Pa.

[73] Assignee: Elf Atochem North America, Inc., Philadelphia, Pa.

[21] Appl. No.: 4,209

[22] Filed: Jan. 13, 1993

Related U.S. Application Data

[63] Continuation-in-part of Ser. No. 748,377, Aug. 22, 1991, abandoned.

[51] Int. Cl.$^6$ .................................... C07C 321/00
[52] U.S. Cl. ............................ 568/26; 568/22
[58] Field of Search .................... 568/21, 22, 26

[56] References Cited

U.S. PATENT DOCUMENTS

| | | | |
|---|---|---|---|
| 2,237,625 | 4/1941 | Olin | 260/125 |
| 3,022,351 | 2/1962 | Mihm et al. | 260/608 |
| 3,392,201 | 7/1968 | Warner | 260/608 |
| 3,755,461 | 8/1973 | Kvasnikoff et al. | 260/608 |
| 4,564,709 | 1/1986 | Koyama et al. | 568/26 |
| 4,876,389 | 10/1989 | Gongora et al. | 568/26 |
| 4,937,385 | 6/1990 | Buchholz et al. | 568/26 |
| 5,026,915 | 6/1991 | Buchholz et al. | 568/26 |
| 5,146,000 | 9/1992 | Ozbalik | 568/26 |

FOREIGN PATENT DOCUMENTS

| | | |
|---|---|---|
| 0337837 | 10/1989 | European Pat. Off. |
| 1162334 | 8/1959 | United Kingdom |

OTHER PUBLICATIONS

Vineyard, B. D., Jour. Organic Chemistry 32, 3833–6 (Dec. 1967).
Rabo, Zeolite Chemistry and Catalysis, ACS, 1976 p. 35.

*Primary Examiner*—Johann Richter
*Assistant Examiner*—Rebecca Cook

[57] ABSTRACT

A process for producing a substantially pure organic trisulfide from mercaptan and sulfur (or high rank organopolysulfide) wherein the sulfur is reacted with mercaptan in the presence of a heterogeneous alumina-based catalyst, ammonium, alkali metal or alkaline earth metal modified silica-based catalyst, zinc-based catalyst or mixtures thereof, and recovering a product containing at least a major proportion of trisulfide.

14 Claims, 2 Drawing Sheets

PROCESS FOR SELECTIVELY PREPARING ORGANIC TRISULFIDES

This is a continuation-in-part of application Ser. No. 07/748,377, filed on Aug. 22, 1991, now abandoned.

BACKGROUND OF THE INVENTION

This invention relates to the selective preparation of organic trisulfides. More particularly, it relates to a process for producing a substantially pure organic trisulfide from mercaptan and sulfur (or a high rank polysulfide as a sulfur source) wherein the sulfur is reacted with mercaptan in the presence of a heterogeneous catalyst which is an alumina-containing material, an alkali metal or alkaline earth metal modified silica, or a zinc oxide-containing material, as defined hereinafter. The process is operated either as a single step batch process, a continuous single-reactor process, or as a final step of a continuous multiple-step process, and may be characterized by the overall reaction illustrated by the following equation (1):

$$2\ RSH + 2\ S \xrightarrow{\text{Catalyst}} RSSSR + H_2S \quad (1)$$

While the above equation demonstrates the stoichiometry of the reaction, surprisingly, in practice, an excess of mercaptan (RSH) is much preferred for efficient production of the pure trisulfide.

Organic polysulfides, for example, t-butyl polysulfides, t-nonyl polysulfides and the like, have excellent extreme-pressure (E.P.), anti-wear and anti-weld properties and are widely used as E.P. additives in lubricant compositions such as metal-working fluids and high pressure gear lubricants. However, polysulfides ($RSS_xSR$, where x is greater than or equal to 2) exhibit high copper-strip corrosivity (ASTM Copper Strip Corrosion Test D-130-56), rendering them unsatisfactory for many commercial lubricating oil applications such as automotive and industrial gear oils. Organic trisulfides, on the other hand, have both optimum sulfur assay and low copper-strip corrosivity making them the ideal E.P. lubricant additives for applications where corrosivity to metals can not be tolerated.

PRIOR ART

The reaction of mercaptans with sulfur in the presence of certain basic catalysts is known for the production of a mixture of polysulfides of varying sulfur rank. U.S. Pat. No. 4,564,709 addresses the selective synthesis of dialkyl trisulfides by reacting sulfur and mercaptan over a magnesium oxide catalyst. The product contains significantly large amounts of tetrasulfide in comparison to the present invention and, in laboratory test operation, the magnesium oxide lost substantially all activity after one batch of material was produced.

U.S. Pat. No. 3,392,201 teaches the production of a product high in alkyl trisulfide by treating a material which contains alkyl trisulfides and alkyl polysulfides (more than 3 sulfur atoms per molecule) with at least one alkali metal hydroxide or ammonium hydroxide whereby the polysulfides are converted to trisulfides.

Vineyard, J. of Org. Chem 32, 3833–6 (1967) and U.K. Patent No. 1,162,334 to Monsanto disclose that an excess of mercaptan is required to react with sulfur for the synthesis of various polysulfides using a liquid amine catalyst. The reaction conditions require the presence of a polar solvent (e.g, methanol) and the trisulfide produced is of low purity.

The above-identified prior art has also failed to recognize the importance of the mercaptan (mole) to sulfur (g-atom) ratio. The preferred ratio range taught in U.S. Pat. No. 4,564,709 is 1.25 to 1.7 while the broad range given is 1.0 to 2.0.

Vineyard teaches that an excess of mercaptan is needed but demonstrates in his working example, that a mercaptan (mole) to sulfur (g-atom) ratio of 1.25 is sufficient.

STATEMENT OF THE INVENTION

This invention is a process for the selective production of organic trisulfides of the formula $R^1SSSR^2$ where $R^1$ and $R^2$ are independently $C_1$ to $C_{24}$ monovalent hydrocarbon radicals optionally having hydroxy or alkoxy substituent groups which process comprises reacting elemental sulfur or a high sulfur rank polysulfide of the formula $$R^1SS_{x-1}SR^2$$

where x is greater than 2 and $R^1$ and $R^2$ are as defined above, with a mercaptan of the structure $R^3SH$, where $R^3$ is the same as $R^1$ and $R^2$, in the presence of a heterogeneous catalyst which is an alumina-containing material, an alkali metal or alkaline earth metal modified silica, or a zinc oxide-containing material, as defined hereinafter and recovering a product containing at least a major proportion of trisulfide.

DETAILED DESCRIPTION OF THE INVENTION

Figure 1:
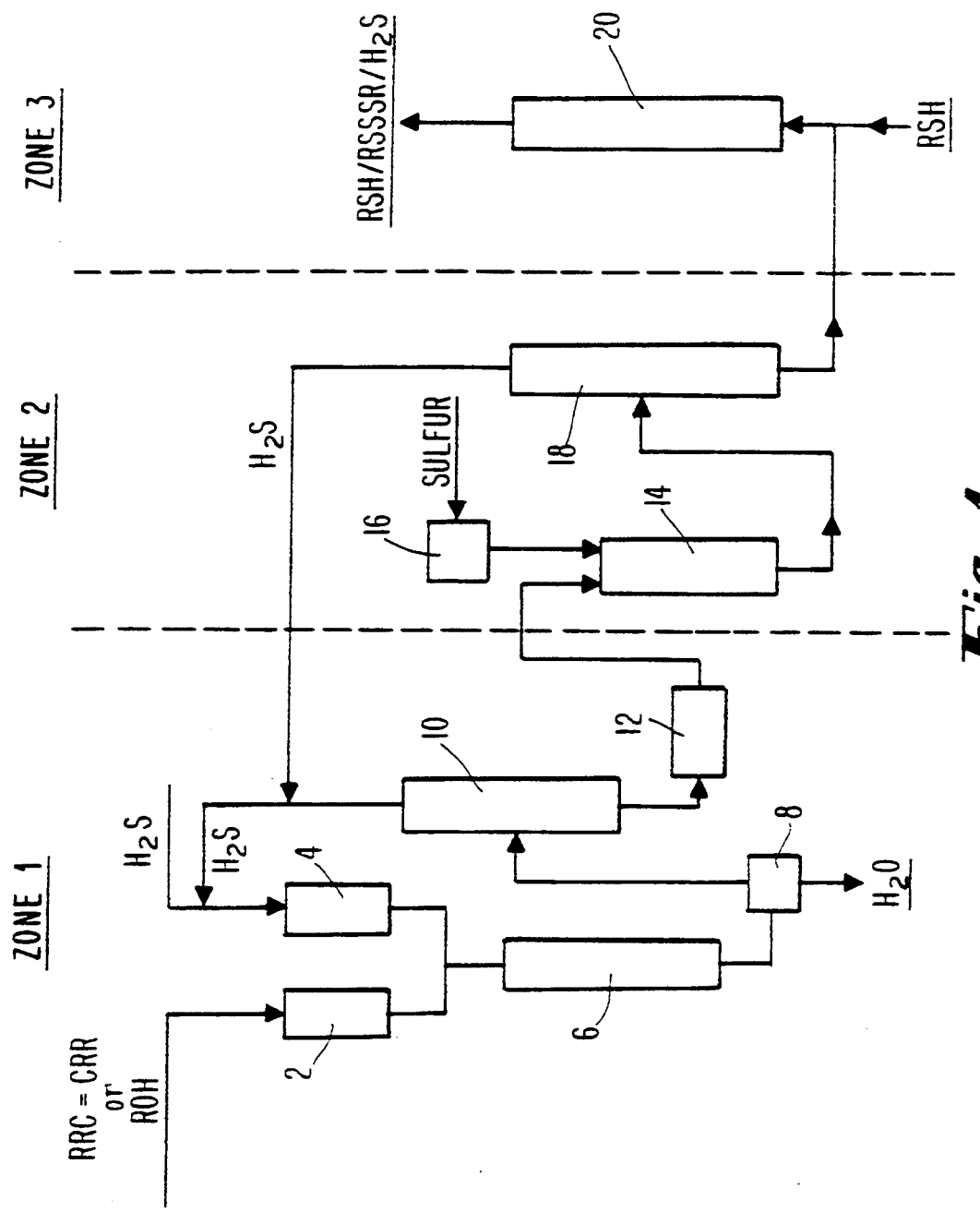
FIG. 1 is a flow diagram for a continuous multi-step embodiment of this invention.

In more detail, this invention is a method for selectively producing an organic trisulfide of the formula $R^1SSSR^2$ where $R^1$ and $R^2$ are independently $C_1$–$C_{24}$ substituted or unsubstituted monovalent hydrocarbon radicals preferably including alkyl, aryl, hydroxy, alkoxy or amino substituted alkyl or aryl groups, or alkaryl groups. More preferably, $R^1$ and $R^2$ are alkyl radicals having 1 to 12 carbon atoms. For example, the alkyl radicals are methyl, ethyl, propyl, butyl, hexyl, octyl, nonyl, decyl and dodecyl groups. The trisulfides are produced by reacting one or more mercaptans having the structure $R^3SH$, where $R^3$ is the same as $R^1$ and $R^2$, with sulfur or a polysulfide of the formula $R^1SS_{x-1}SR^2$, where x is greater than 2, in the presence of a heterogeneous (insoluble in the reaction mixture) catalyst which is an alumina-containing material, alkali metal or alkaline earth metal modified silica, or a zinc oxide-containing material, as defined hereinafter, and recovering a product which is at least a major proportion of trisulfide relative to the total weight of other sulfides in the product. Preferably, at least about 70% by weight of the product is trisulfide.

The letter x in the above formula represents the average number of internal sulfurs in a given organopolysulfide composition and not the maximum number of sulfur atoms for any one species of polysulfide in the composition. The term "high rank" polysulfide refers to compounds or mixtures of compounds wherein the polysulfide contains labile sulfur atoms and where x in the above formula is greater than 2.

The selective production of pure trisulfides, as opposed to a product having a distribution of disulfide, trisulfide, tetrasulfide, etc., is not overly discussed in the relevant prior art, patent references U.K. Patent No. 1,162,334, U.S. Pat. Nos. 4,564,709 and 3,339,201 being exceptions. The present invention not only provides a method for selectively producing organotrisulfides but also furnishes the capability of yielding material of a selected distribution of disulfide, trisulfide and tetrasulfide. A selective distribution of di-, tri- and tetra-polysulfides can be produced by controlling the process conditions. High disulfide levels are favored by higher temperature, increased mercaptan to sulfur ratios, and longer residence times in Zone 2 while temperature and residence time control the amount of disulfide produced in Zone 3 of the accompanying drawing. The level of tetrasulfide desired is controlled by selecting the proper mercaptan to sulfur ratio in Zone 3. Higher values for this ratio produce lower levels of tetrasulfide. For example, if one wanted a distribution containing a high disulfide level and a high tetrasulfide level then the conditions employed in Zone 3 would be high temperature and low mercaptan to sulfur ratio. However, if low disulfide and low tetrasulfide levels are desired then a low temperature and a high mercaptan to sulfur ratio would be employed.

In general, the range of amounts of organic trisulfide which is produced in the process of this invention is between about 70 to 99 weight percent of the product. The organic disulfide which is coproduced ranges from about 0.1 to 29.9 while the range of tetrasulfide (and higher sulfur rank polysulfides) will also range from 0.1 to 29.9, the total of the sulfides equaling 100%

As previously stated, the overall reaction of this process is illustrated by equation (1)

$$2\ RSH + 2\ S \xrightarrow{Catalyst} RSSSR + H_2S \quad (1)$$

When the progress of the reaction is followed as a function of time, it is observed that two parallel reactions take place; a fast reaction, as shown in equation (2), produces mostly high rank (x>2) polysulfides and the largest portion of H$_2$S

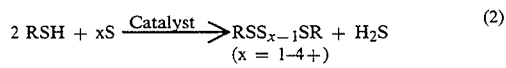

$$2\ RSH + xS \xrightarrow{Catalyst} RSS_{x-1}SR + H_2S \quad (2)$$
$$(x = 1-4+)$$

and a slow reaction, as shown in equation (3), which consumes the high rank (x>2) polysulfides of equation (2), producing predominantly trisulfide.

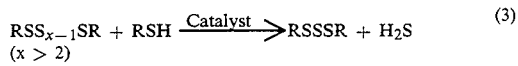

$$RSS_{x-1}SR + RSH \xrightarrow{Catalyst} RSSSR + H_2S \quad (3)$$
$$(x > 2)$$

If the reaction is not stopped upon completion of the reaction of equation (3), then the trisulfide (RSSSR) will be converted to the disulfide (RSSR) as shown in equation (4)

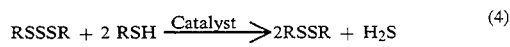

$$RSSSR + 2\ RSH \xrightarrow{Catalyst} 2RSSR + H_2S \quad (4)$$

Accordingly, the reaction of equation (3) is carried out for a time sufficient to produce trisulfides and terminated before the formation of appreciable quantities of disulfides as in equation (4). The period of time for the production of a predominent amount of trisulfides and before the formation of appreciable amounts of disulfide will vary greatly depending on the reactor design and reaction conditions employed. However, under each set of conditions the time element may be readily determined empirically by periodic sampling and analysis of the product.

An important aspect of this invention, if very pure trisulfide is desired, is the disengagement of H$_2$S (hydrogen sulfide) produced from the reaction of mercaptan with sulfur. This is required to force the reaction, as illustrated by equation (3), to completion. The removal of H$_2$S from the reactor may be accomplished, for example, by purging the reaction mixture with an inert gas, cycling the reaction mixture through a pressure drop, spraying the mixture on a heated surface with a large surface area, or by refluxing the reaction mixture.

As previously mentioned, the process of the invention can either be operated as a single step, batch process, a continuous, single reactor process or as the final step of a continuous, multi-step process with separate reaction conditions in each reaction zone.

CATALYST DESCRIPTION

The catalyst used for the trisulfide producing reaction in any of the above-described process types is a heterogeneous catalyst which is (i) an alumina-containing material which, for the purpose of this disclosure, is limited to alumina alone; titania, silica and alumina mixtures; titania and alumina mixtures; and silica (including alkali and alkaline earth metal modified silica) and alumina mixtures, such mixtures optionally containing up to 25 weight percent of other elements, compounds or complexes including, for example, phosphorous oxide, thoria, alkali metal tungstate, chromia, zeolites and the like; (ii) silica which contains at least 0.5 weight percent of sodium, potassium, calcium or magnesium, but silica alone, which is not modified by one of these basic metals, shows relatively slight activity and is excluded; or (iii) zinc oxide alone or in mixtures with one or more of titania, alumina and silica (or modified silica as defined above), the zinc oxide or disclosed mixtures thereof optionally including up to 25 weight percent of the elements, compound or complexes mentioned above for the alumina-containing material. Zeolites, except the acidic Type Y synthetic zeolites, are included within the catalysts of this invention so long as they meet the above catalyst description regarding metal or metal compound content.

All of the catalysts referred to above are effective for the process described herein but the preferred are zinc oxide-alumina, zinc oxide-silica-alumina and titania-silica-alumina. The activity of various catalysts differs mainly in the ability of a selected catalyst to produce a trisulfide with both a very low tetrasulfide content (less than 1 wt. %) and a low disulfide content (less than 5 wt. %).

The ratio of mercaptan (moles) to sulfur can range from 1.0 to 10.0 depending on the purity of product desired. For example, in the case of t-butyl trisulfide, if a very pure product is desired, then the preferred range lies between 3 and 10 and more preferably between 5 and 10. In general, the preferred range is between 1.7 and 10. Material produced within this range has the lowest residual tetrasulfide content. When a high rank polysulfide is used as the sulfur source, the amount of mercaptan used is adjusted to the amount of sulfur generated by the polysulfide to fit within the above-described mercaptan (moles) to sulfur (g-atom) ratio range.

The prior art suggests that a very high mercaptan to sulfur ratio is undesirable because large amounts of disulfide would be produced under these conditions. This would be true if the reaction were not stopped in time as described above, However, the mercaptan to sulfur ratio controls the point where the minimum level of high rank ($x>2$) polysulfide is achieved before significant amounts of organic disulfide are produced. For example, if t-butyl mercaptan is reacted with sulfur at a molar ratio of 1.7, the minimum level of t-butyl tetrasulfide produced before significant quantities of t-butyl disulfide are generated, is about 5%. However, if under the same conditions a mercaptan to sulfur molar ratio of 5 is employed, then the minimum level of t-butyl tetrasulfide achievable is less than 1% before significant quantities of t-butyl disulfide are generated. This realization is completely unobvious in view of the disclosure of the prior art relative to mercaptan to sulfur ratio.

The temperature range of the process is generally between about 30° and 120° C., preferably between about 35° and 100° C. Of course, the temperature in these systems is limited by the pressure limitation of the reaction vessel and the reflux temperature of the reaction medium. The most preferred method of operation, independent of the type of reactor used, is at reflux temperature of the reaction medium, provided the reactants and products are stable at this temperature. If a volatile mercaptan is employed, the reaction can be operated first at a lower temperature, where the initial stages of the reaction occurs and the largest majority hydrogen sulfide is evolved, and then at higher temperature within the prescribed range to complete the conversion of high rank ($x>2$) polysulfides to trisulfide. This will reduce the loss of the volatile mercaptan. The temperature in the reaction zone in a continuous-multiple reactor process, where the catalyst bed comprises an alumina-containing material, ranges from about 30° to about 120° C.; preferably between 35° and 100° C.

The temperature is a critical parameter in controlling the distribution of the trisulfide. If for example, one desires material with a high level of disulfide within the parameters of the polysulfide composition of the invention, then a high temperature (80°–120° C.) would be chosen. However, if a low disulfide material is desired, then a lower temperature would be chosen.

The residence time of the reaction medium is clearly defined as the length of time necessary to permit recovery of a product containing at least 70 weight percent organic trisulfide. Typical ranges are provided below to better teach how residence time impacts the production of trisulfides, but are not intended to limit the invention. In addition, the residence time depends greatly on the distribution desired and the temperature of the reaction. If a high temperature is employed, and a limited amount of disulfide is desired, then the residence time of the reaction medium will range from approximately 1 minute to 1 hour depending on the level of tetrasulfide desired. However, the residence time must be controlled carefully to avoid large amounts of disulfide. If lower temperatures are used, then the residence time will range from approximately 5 minutes to 5 hours depending on the level of tetrasulfide desired. High levels of disulfides are avoided at lower temperatures. Of course, the amount of catalyst used will vary the residence time required.

Conditions most favorable to the production of pure tertiary (t)-$C_4$-$C_{12}$ alkyl trisulfide may be summarized as follows:

Temperature: 35°–70° C.
Pressure: 0.015 psia (pounds per square inch absolute) to 250 psig (pounds per square inch gauge)
Reactant Ratio: 5–10 moles of mercaptan for each g-atom of sulfur contributed by the high sulfur rank polysulfide.
Reaction (Residence) Time: about 10 minutes to 6 hours In any of the reactor processes, the reaction pressure in the mercaptan-sulfur reaction zone ranges from ambient to about 300 psig, preferably from ambient to 250 psig. A lower pressure, within this range, is preferred depending on the volatility of the mercaptan. Operation of the process at a pressure at which the $H_2S$ evolved is dissolved in the liquid phase is advantageous.

In the process of this invention, a polar solvent such as methanol, as required in the process of Vineyard, supra, is not needed to produce pure trisulfide product. In addition, catalyst deactivation is not observed as for the magnesium oxide catalyst of U.S. Pat. No. 4,564,709.

The type of reactor chosen for operation of the process in a continuous, single step depends on the reaction conditions desired and whether sulfur or a high rank ($x>2$) polysulfide is used as the sulfur source. If sulfur is used, and the reaction temperature is below the melting point of sulfur, then a continuous-stirred-tank-reactor is required. If a high rank ($x>2$) polysulfide is employed, then a fixed-bed reactor can be utilized.

When the use of a continuous, multiple-step reactor process is contemplated, organic trisulfides are produced from a starting alcohol ($R^8OH$) or olefin ($R^4R^5C=CR^6R^7$) reacted with $H_2S$ and sulfur, the resultant high rank ($x>2$) polysulfide is then converted to the trisulfide by a controlled reaction with a mercaptan. $R^4$-$R^7$ for the above olefin formula are hydrogen or as described for $R^1$ and $R^2$. The olefin used does not necessarily need to be a pure olefin. For example, t-nonyl mercaptan is often prepared using an olefin mixture which is a distillation cut from the trimerization of propylene. This mixture typically contains olefins ranging from 8–10 carbons. Likewise, t-dodecyl mercaptan is often prepared from an olefin mixture which is a distillation cut from the tetramerization of propylene. This mixture is also a distillation cut which contains olefins ranging from 9 carbons to 14 carbons. $R^8$ for the above alcohol formula is as described for $R^1$ and $R^2$. The alcohol or olefin and $H_2S$ are reacted in a first reaction zone to form crude mercaptan; the mercaptan-containing reactor effluent is stripped of $H_2S$ (and water removed, if present) and then passed directly into a second reaction zone where it is reacted with sulfur to produce an organic polysulfide of high sulfur rank ($x>2$). Depending on the purity of the product desired and the conversion of the mercaptan being produced, the mercaptan may or may not require further purification. The intermediate polysulfide is then reacted with additional mercaptan to produce a pure organic trisulfide in a third reaction zone, the reaction with mercaptan generally terminating with the formation of the trisulfide and before any formation of substantial amounts of disulfide.

Further details of the continuous, multiple step process are seen in the accompanying drawing wherein FIG. 1 is a flow diagram of the continuous, multiple-step process. In Zone 1 of FIG. 1, an olefin or an alcohol is fed continuously through preheater 2 and H₂S is fed continuously through preheater 4 to a first reactor 6 to produce a crude mercaptan from which water (if initial reactant is an alcohol) is removed in liquid-phase water separator 8. The crude mercaptan is then passed to a high-pressure separator 10 from which a major portion of the residual H₂S is removed overhead and recycled back to preheater 4. The effluent removed from the bottom of separator 10, consisting of crude mercaptan and residual H₂S, is passed through preheater 12 into reactor 14 of Zone 2. Sulfur is charged to reactor 14 via preheater 16 and the formed crude high rank polysulfide is passed from the bottom of reactor 14 to distillation column 18 where H₂S is removed overhead and recycled to preheater 4. The bottoms stream from distillation column 18 is passed to reactor 20 of Zone 3 containing a catalyst of this invention. Any additional mercaptan required to adjust the overall mercaptan (mole) to sulfur (g-atom) ratio, as prescribed, is also supplied at the bottom of reactor 20. In reactor 20, the high rank (x>2) polysulfides are converted to pure trisulfide in accordance with this invention and as represented by equation (3), and then discharged overhead from reactor 20. The preferred equipment for Zone 3 is a fixed-bed, up-flow-reactor. However, other equipment can be used including, for example, fixed-bed, down-flow; continuous-stirred-tank (CSTR); external transport; or other reactor designs similar to those used in reactive distillation processes.

The reactions of Zones 1 and 2 are more fully described in U.S. Pat. No. 5,026,915, and U.S. Pat. No. 4,937,385. The processes disclosed in these patents are incorporated herein by reference.

Figure 2:
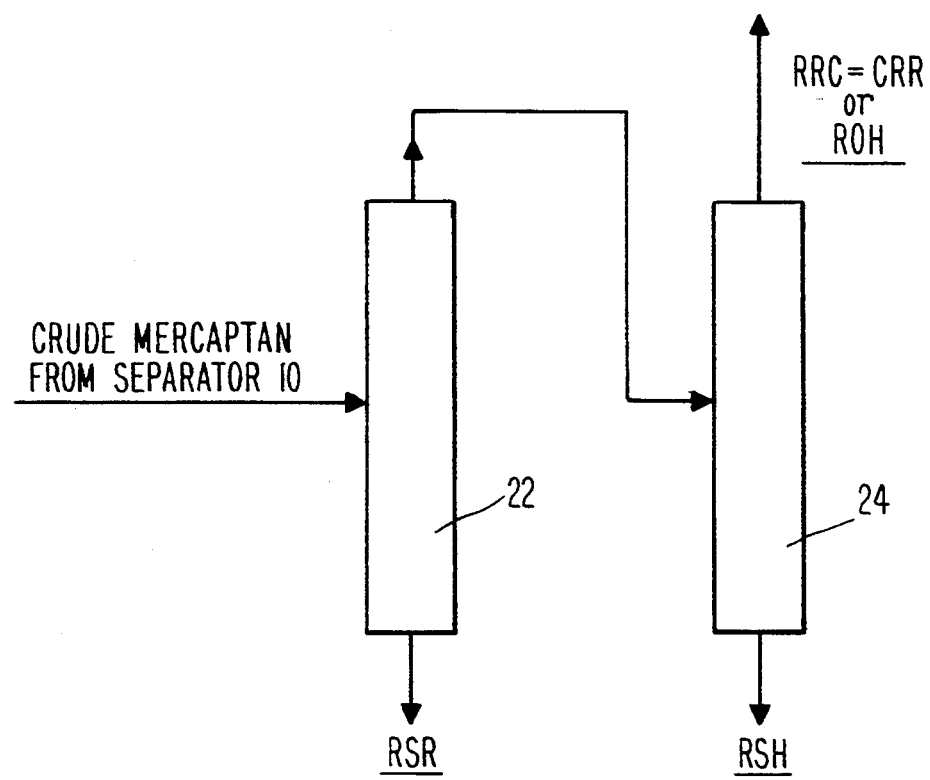
FIG. 2 shows a series of distillation towers which may be used for purification of crude mercaptan produced in Zone 1 of FIG. 1.

In FIG. 2, a system is shown which may be used to further purify the crude mercaptan effluent from high-pressure separator 10, if necessary. Crude mercaptan from separator 10 is directed to distillation tower 22 of FIG. 2 where the mercaptan and excess alcohol or olefin (overhead distillate) are separated from organosulfide (bottoms). The olefin or alcohol (overhead) is then separated from the mercaptan (bottoms) in distillation tower 24. The olefin or alcohol is recycled to reactor 6 via preheater 2 of Zone 1 and the mercaptan is passed to reactor 14 of Zone 2.

Figure 3:
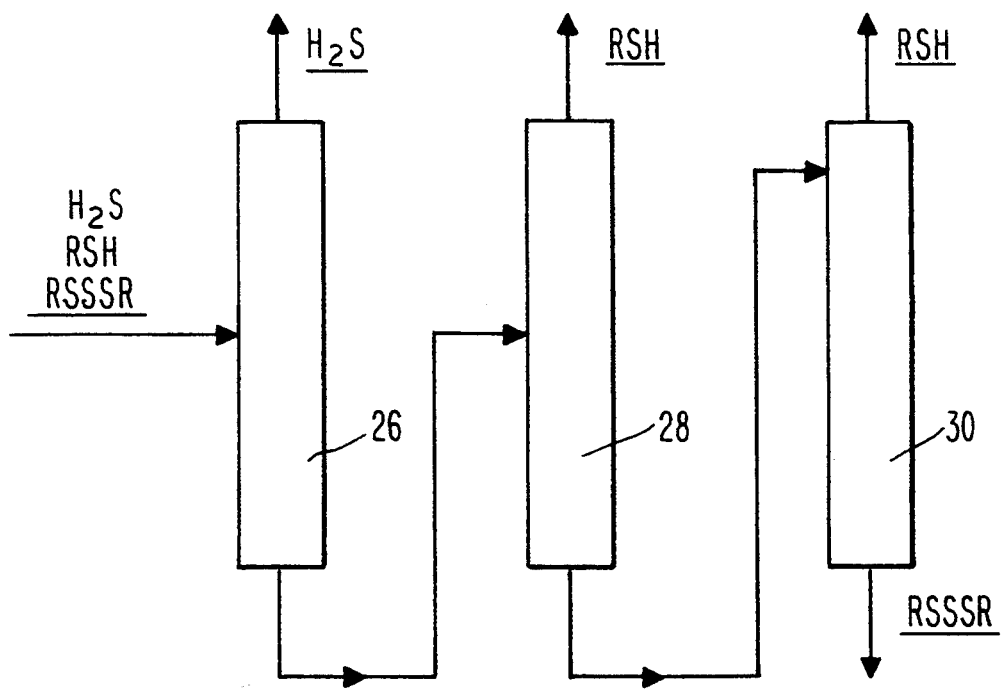
FIG. 3 is a second series of distillation towers for the removal of $H_2S$, and mercaptan from pure organic trisulfide produced in Zone 3 of FIG. 1.

To separate the pure trisulfide product of reactor 20 (Zone 3) from H₂S and mercaptan, the overhead from reactor 20 may be passed to distillation tower 26 of FIG. 3 where H₂S is removed overhead and recycled to reactor 6 via preheater 4. The bottoms product of tower 26 is then sent to distillation tower 28 where the majority of mercaptan is removed overhead and recycled to reactor 14. The bottoms product of tower 28 is then passed to vacuum distillation tower 30 for the overhead removal of the last traces of residual mercaptan which also may be recycled, if desired. Pure trisulfide is recovered from the bottom of tower 30.

While the flow diagram of FIG. 1 describes a continuous process, a batch process could also be utilized in Zone 1, Zone 2 and/or Zone 3, if desired.

The following examples are set forth to demonstrate the operation of the process of this invention.

EXAMPLE 1

Di-tert-Butyl Trisulfide—Batch Process

The apparatus used for this work consisted of a 100 ml, 3-necked round bottom flask equipped with a temperature controlled heating mantle and magnetic stirrer. Fitted to the flask were a thermocouple well, a septum inlet with stopcock, and a glycol cooled (10° C.) condenser. The vent from the condenser was connected to a burner line for odor control.

The reactor flask was charged with the desired catalyst and sulfur at a ratio (by weight) of approximately 3.3 and sealed. Via the septum inlet, t-butyl mercaptan was then added and the mixture was heated to reflux with stirring. Samples were taken at various intervals and analyzed by gas chromatography. Table 1 shows the results for a variety of catalysts and conditions used in runs 1–17. All runs were carried out at atmospheric pressure.

Runs 1–8 show the effectiveness of a variety of alumina-based catalysts.

Run 9 shows the effectiveness of silica with sodium content greater than 0.5% as a catalyst.

Runs 10–11 show the effectiveness of zinc-based catalysts.

Runs 12–15 show the effect of the mercaptan (mole) to sulfur (g-atom) ratio on the purity of the trisulfide.

Runs 16–17 show the effect of the removal of hydrogen sulfide by reflux on the reaction. Run 17 was conducted at 54° C. which is below the reflux temperature (65° C.) of the reaction mixture. All other runs were conducted at the reflux temperature. After 40 minutes, the minimum level of tetrasulfide obtained in run 17 was 1.5% versus 0.5% obtained after 30 minutes at reflux (Run 16).

TABLE 1

| Run | Catalyst Type | Catalyst Identity (Supplier-Grade No.) | TBM/S Ratio | TIME (min) | % POLYSULFIDE* | | |
|---|---|---|---|---|---|---|---|
| | | | | | TBS2 | TBS3 | TBS4 |
| 1 | Alumina | Harshaw Alumina AL0184T 1/8 | 5 | 30 | 1.15 | 97.10 | 1.76 |
| 2 | Alumina | Harshaw Alumina AL3996R LOT H-27 | 5 | 30 | 1.30 | 97.40 | 1.35 |
| 3 | Alumina | Harshaw Alumina AL-3438 LOT34 DRUM29 | 5 | 90 | 1.42 | 97.2 | 1.37 |
| 4 | Alumina | Akzo Gamma Alumina 000-3P | 5 | 30 | 3.1 | 96.4 | 0.5 |
| 5 | Alumina | Davison High SA Alumina Spheres SSMR 7-6454 | 5 | 20 | 2.9 | 96.6 | 0.5 |
| 6 | Titania-Silica-Alumina | Harshaw Alumina AL-50002 | 5 | 20 | 2.5 | 97 | 0.5 |

TABLE 1-continued

| Run | Catalyst Type | Catalyst Identity (Supplier-Grade No.) | TBM/S Ratio | TIME (min) | % POLYSULFIDE* TBS2 | TBS3 | TBS4 |
|---|---|---|---|---|---|---|---|
| 7 | Titania-Alumina | Harshaw 539A-10-1-21 | 5 | 20 | 3 | 96.4 | 0.7 |
| 8 | Silica-Alumina | Harshaw 539A-22-46-21 | 5 | 20 | 2.3 | 96.9 | 0.8 |
| 9 | Silica-Based | Silica + 3% Na | 3 | 45 | 0.8 | 91 | 8.2 |
| 10 | Zinc-Alumina | Harshaw 377A-2-1-16 | 5 | 30 | 5.3 | 94.2 | 0.5 |
| 11 | Zinc-Based | Zinc Oxide | 5 | 30 | 4.8 | 95 | 0.2 |
| 12 | Zinc-Alumina | Harshaw 377A-2-1-16 | 5 | 30 | 5.3 | 94.2 | 0.5 |
| 13 | Zinc-Alumina | Harshaw 377A-2-1-16 | 1.7 | 30 | 32.5 | 62.6 | 4.9 |
| 14 | Titania-Silica-Alumina | Harshaw Alumina AL-5002 | 5 | 20 | 2.5 | 97 | 0.5 |
| 15 | Titania-Silica-Alumina | Harshaw Alumina AL-5002 | 1.7 | 30 | 28.3 | 57.3 | 14.2 |
| 16 | Zinc-Alumina | Harshaw 377A-2-1-16 | 5 | 30 | 5.3 | 94.2 | 0.5 |
| 17 | Zinc-Alumina | Harshaw 377A-2-1-16 | 5 | 40 | 2.9 | 95.8 | 1.8 |

*Ratio of t-butyl mercaptan (mole) to sulfur (g-atom)
**Area percent of t-butyl disulfide, t-butyl trisulfide and t-butyl tetrasulfide based on gas chromatographic analysis. (mercaptan-free)

In comparison to the foregoing results, several experiments were performed to demonstrate relevant prior art processes.

Experiment A

Di-tert-butyl Trisulfide—Using an Amine Catalyst, a Mercaptan (mole) to Sulfur (g-atom) Ratio of 5.0, and Methanol as a Solvent.

This example illustrates the inability of amine catalysts of the prior art to produce high purity trisulfides from mercaptans and sulfur.

The apparatus used for this work consisted of the same equipment used in Example 1.

The reactor flask was charged with 1.23 g of sulfur. Via the septum inlet, 16.9 g of t-butyl mercaptan, 4.76 ml of methanol, and 0.075 ml of t-butyl amine were then added and the mixture was heated to reflux with stirring for 4 hours. Analysis by gas chromatography, showed the levels of tert-butyl disulfide, tert-butyl trisulfide, and tert-butyl tetrasulfide to be 0.28%, 88.84%, and 10.86%, respectively, on a mercaptan-free basis.

Experiment B

Di-tert-Butyl Trisulfide—Using Magnesium Oxide as a Catalyst

This example shows that magnesium oxide is an effective catalyst for producing pure trisulfides (Prior Art); however, this catalyst loses activity after one run.

The apparatus used for this work consisted of the same equipment used in Example 1.

The reactor flask was charged with 1.9971 g of sulfur and 0.2535 g of magnesium oxide and sealed. Via the septum inlet, 28 g of t-butyl mercaptan were then added and the mixture was heated to reflux and stirred for 5 hours. The reaction mixture was sampled after 1.5 hours and analysis by gas chromatography, showed the levels of tert-butyl disulfide, tert-butyl trisulfide, and tert-butyl tetrasulfide to be 1.12%, 97.6%, and 1.27%, respectively, on a mercaptan-free basis. Analysis of reaction mixture after 5 hours by gas chromatography, showed the levels of tert-butyl disulfide, tert-butyl trisulfide, and tert-butyl tetrasulfide to be 2.5%, 96.5% and 0.89%, respectively, on a mercaptan-free basis.

The mixture was allowed to cool and settle overnight. The liquid was carefully removed and the procedure was repeated using the same magnesium oxide. No reaction was observed.

Runs 18–23 of Table 1A demonstrate that the class of catalysts of this invention do not lose activity after one run as was the case with magnesium oxide. The same charge of catalyst was used successively for Runs 18–23 by carefully removing the reaction mixture at the end of each run after the catalyst had been given sufficient time to settle. The apparatus used was the same equipment used in Example 1. The catalyst was Harshaw 377A-2-1-16, a zinc-alumina, and the t-butyl mercaptan to sulfur ratio was 5 in each run.

TABLE 1A

| RUN | Time (min) | % Polysulfide TBS2 | TBS3 | TBS4 |
|---|---|---|---|---|
| 18 | 25 | 7.6 | 92.0 | 0.4 |
| 19 | 25 | 9.3 | 90.3 | 0.4 |
| 20 | 25 | 11.8 | 87.9 | 0.5 |
| 21 | 25 | 7.9 | 87.9 | 0.8 |
| 22 | 20 | 7.6 | 87.9 | 1.5 |
| 23 | 20 | 6.5 | 90.4 | 0.9 |

EXAMPLE 2

Di-tert-Butyl Trisulfide—Batch Process using tert-Butyl Polysulfide in Lieu of Sulfur.

The apparatus used for this work consisted of the same equipment used in Example 1.

The reactor flask was charged with the 4.0 g of the desired catalyst and sealed. Via the septum inlet, 5.9 g of t-butyl mercaptan and 3.2 g of t-butyl polysulfide[1] were added and the mixture was heated to reflux with stirring. Samples were taken at various intervals and analyzed by gas chromatography. The results are presented in Table 2.

[1] The t-butyl polysulfide used as feed stock for this Example contained 5.2% t-butyl disulfide, 60.2% t-butyl trisulfide and 34.6% t-butyl tetrasulfide based on gas chromatography analysis.

TABLE 2

| Run | Catalyst Type | Catalyst Identity (Supplier-Grade No.) | TBM/S Ratio | TIME (min) | % POLYSULFIDE* | | |
|---|---|---|---|---|---|---|---|
| | | | | | TBS2 | TBS3 | TBS4 |
| 1 | Alumina | Davison Alumina SMR-7-6454 | 5 | 20 | 4.4 | 95.2 | 0.4 |
| 2 | Zinc-Alumina | Harshaw 377A-2-1-16 | 5 | 25 | 4.5 | 94.6 | 0.8 |
| 3 | Silica-Alumina | Harshaw AL-539A-22-46-21 | 5 | 20 | 5.52 | 93.38 | 1.09 |
| 4 | Titania-Silica-Alumina | Harshaw AL-5002E | 5 | 25 | 5.85 | 93.43 | 0.72 |

*Area percent of t-butyl disulfide, t-butyl trisulfide and t-butyl tetrasulfide based on gas chromatographic analysis (mercaptan free)

EXAMPLE 3

Di-tert-Butyl Trisulfide—Continuous Process

Tert-butyl mercaptan, sulfur, and hydrogen sulfide were passed through a 1.5-inch fixed-bed reactor containing 100 g UOP's LX-Y52 zeolite at molar velocities of 1,000, 700, and 200, respectively. The temperature of the reactor was 130° C. and the pressure was 350 psig. The reactor effluent was collected in a stainless-steel cylinder at 25° C. and 100 psig. Analysis by gas chromatography, showed the levels of tert-butyl disulfide, tert-butyl trisulfide, and tert-butyl tetrasulfide to be 1.4%, 54.5%, and 44.1%, respectively, on a mercaptan-free basis.

The collected reactor effluent (di-tert-butyl polysulfide and tert-butyl mercaptan) and additional tert-butyl mercaptan were then passed through a one-inch fixed-bed reactor containing 57.7 g of Harshaw's Zinc-Alumina (377A) in an up-flow direction at 0.45 g/min and 0.6 g/min, respectively. The temperature of the reactor was at 60° C. and the pressure was ambient. Analysis of the reactor effluent by gas chromatography, showed the levels of tert-butyl disulfide, tert-butyl trisulfide, and tert-butyl tetrasulfide to be 3%, 93.7%, and 2.1% respectively, on a mercaptan-free basis.

Similar excellent results for the preparation of a product containing almost pure t-nonyl trisulfide or t-dodecyl trisulfide can be obtained using the same equipment and procedure as described in Example 3 with either a t-nonyl mercaptan or t-dodecyl mercaptan starting reactant in place of t-butyl mercaptan.

EXAMPLE 4

Di-tert-Butyl Trisulfide—Continuous Process

T-butyl mercaptan and sulfur were passed through an 70 inch long by 1.03 inch ID adiabatic tubular reactor containing 495 g of UoP's LZ-Y52 zeolite, a sodium type Y synthetic zeolite, at molar velocities of 6,000 and 3,000, respectively. The temperature of the reactor was 130° C. and the pressure was 200 psig. The reactor effluent was collected in a 10 inch ID by 24 inch straight-side vertical liquid/vapor separator. Analysis by gas chromatography, showed the levels of t-butyl disulfide, t-butyl trisulfide, and t-butyl tetrasulfide to be 3.1%, 52.5%, and 44.3%, respectively, on a mercaptan-free basis.

The collected reactor effluent (di-t-butyl polysulfide and t-butyl mercaptan) and t-butyl mercaptan were then passed through a 96 inch long by 2 inch ID tubular adiabatic reactor, containing 4.45 kg of Harshaw's Zinc Oxide-Alumina (337A) at rates of 61.7 g/min and 83.3 g/min, respectively. The temperature of the reactor was 50° C. and the pressure was 184 psig. Analysis of the reactor effluent by gas chromatography, showed the levels of t-butyl disulfide, t-butyl trisulfide, and t-butyl tetrasulfide to be 2.8%, 94.8%, and 2.4%, respectively, on a mercaptan-free basis

We claim:

1. A process for the selective production of organic trisulfides of the formula $R^1SSSR^2$ where $R^1$ and $R^2$ are independently $C_1$–$C_{24}$ monovalent hydrocarbon radicals optionally having hydroxy or alkoxy substituent groups, said process comprising reacting in the absence of a polar solvent a first high sulfur rank polysulfide as the major sulfur source of the reaction, said polysulfide having the formula $R^1SS_{x-1}SR^2$ where x is greater than 2 and $R^1$ and $R^2$ are as defined above, with an excess of a mercaptan of the structure $R^3SH$, where $R^3$ is of the same description as $R^1$ and $R^2$, at a reaction temperature ranging from about 30° to 120° C. and in the presence of a heterogeneous catalyst which is a) an alumina-containing material, b) silica modified with at least 0.5 weight percent of either sodium, potassium, calcium or magnesium, or c) a zinc oxide-containing material, each of the recited catalysts being different in composition than the others, and terminating the reaction in sufficient time to permit recovery of a total product containing at least 70 weight percent of organic trisulfide of the above formula, at least a portion of which is the product of the reaction of said first high sulfur rank polysulfide and said mercaptan.

2. The process of claim 1 wherein said monovalent hydrocarbon radical is alkyl, aryl or alkaryl.

3. The process of claim 2 wherein the process is carried out in the presence of a catalyst which is an alumina-containing material.

4. The process of claim 2 wherein the process is carried out in the presence of a catalyst which is alumina, zinc oxide-alumina or titania-silica-alumina.

5. The process of claim 1 wherein said first high sulfur rank polysulfide is earlier prepared by reacting a mercaptan of the formula $R^3SH$ wherein $R^3$ is of the same description as $R^1$ and $R^2$ with elemental sulfur or a polysulfide of higher sulfur rank than said first polysulfide in the presence of a solid particulate catalyst.

6. The process of claim 5 wherein said mercaptan is prepared by reacting an olefin or alcohol corresponding to said mercaptan with hydrogen sulfide in the presence of a catalyst.

7. The process of claim 5 where, in the reaction for the production of trisulfide, $R^1$ and $R^2$ are alkyl radicals having 1 to 12 carbon atoms, the reaction ratio ranges between 1.7 to 10 moles of mercaptan to each g-atom of sulfur contributed by said first polysulfide, said reaction temperature ranges from 35° to 100° C., and the reaction pressure ranges between 0.015 psia to about 250 psig.

8. The process of claim 7 wherein the reaction for the production of trisulfide is carried out in the presence of a catalyst which is an alumina-containing material.

9. The process of claim 7 wherein said "alumina-containing material is alumina, zinc oxide-alumina, or titania-silica-alumina.

10. A process for the selective production of t-butyl, t-nonyl or t-dodecyl trisulfide which comprises reacting in the absence of a polar solvent, a first high sulfur rank polysulfide as the major sulfur source of the reaction, said polysulfide having the formula $$R^1SS_{x-1}SR^2$$

where $R^1$ and $R^2$ are t-butyl, t-nonyl or t-dodecyl and x is greater than 2, with its corresponding t-alkyl mercaptan at a reaction temperature ranging between 35° and 100° C., a reaction pressure ranging between about 0.015 psia and about 250 psig and at a reactant ratio of from 1.7 to 10 moles of mercaptan for each g-atom of sulfur contributed by said first polysulfide in the presence of a heterogeneous catalyst material which is alumina, zinc oxide-alumina, zinc oxide-silica-alumina, or titania-silica-alumina, and terminating the reaction in sufficient time to recover a total product containing at least 70 weight percent of the corresponding t-alkyl trisulfide at least a portion of which is the product of the reaction of said first high sulfur rank polysulfide and said mercaptan.

11. The process of claim 10 wherein said first sulfur rank polysulfide is earlier prepared by reacting a mercaptan of the formula $R^3SH$ wherein $R^3$ is t-butyl, t-nonyl or t-dodecyl with elemental sulfur or a polysulfide of higher sulfur rank than said first polysulfide in the presence of a solid, particular catalyst.

12. The process of claim 11 wherein said mercaptan is prepared by reacting an olefin or alcohol corresponding to said mercaptan with hydrogen sulfide in the presence of a catalyst.

13. The process of claim 11 wherein any hydrogen sulfide generated during the preparation of said first polysulfide is removed from the presence of said first polysulfide before said polysulfide is used to prepare organic trisulfide.

14. The process for selective production of t-butyl trisulfide which comprises reacting in the absence of a polar solvent, a high sulfur rank polysulfide as the major sulfur source of the reaction, said polysulfide having the formula $$R^1SS_{x-1}SR^2$$

where $R^1$ and $R^2$ are t-butyl and x is greater than 2, with t-butyl mercaptan at a reaction temperature ranging between 35° and 70° C., a reaction pressure ranging between about 5 psia and about 250 psig, at a reactant ratio of from 5 to 10 moles of mercaptan to each g-atom of sulfur contributed by said polysulfide, for a time ranging from about 5 minutes to about 6 hours, and in the presence of a heterogeneous catalyst material which is alumina, zinc oxide-alumina, or titania-silica-alumina, and continuously removing any $H_2S$ as it is formed during the reaction.

* * * * *